United States Patent [19]

Linyaev et al.

[11] Patent Number: 4,928,031
[45] Date of Patent: May 22, 1990

[54] PRESSURE/TEMPERATURE COMPENSATED TRANSDUCER PAD ASSEMBLY

[75] Inventors: Eugene J. Linyaev, Houston; Roy E. Swanson, Jr., Sugarland, both of Tex.

[73] Assignee: Western Atlas International, Inc., Houston, Tex.

[21] Appl. No.: 934,672

[22] Filed: Nov. 25, 1986

[51] Int. Cl.⁵ ............................................. H01L 41/08
[52] U.S. Cl. .................................... 310/346; 310/344
[58] Field of Search ............................. 310/340–346; 174/12 R; 340/853; 73/151, 431, DIG. 4; 367/25, 911, 912; 175/50; 92/261; 166/336, 360, 248–250, 65.1, 66, 177, 324, 332, 243

[56] References Cited

U.S. PATENT DOCUMENTS

| | | | |
|---|---|---|---|
| 3,123,784 | 3/1964 | Ritz | 174/12 R |
| 3,243,496 | 3/1966 | Silverstein | 174/12 R |
| 4,092,484 | 5/1978 | Majkrzak et al. | 174/12 R |
| 4,331,830 | 5/1982 | Conway et al. | 174/12 R |

FOREIGN PATENT DOCUMENTS 1305905  2/1973  United Kingdom ............. 174/12 R

Primary Examiner—Mark O. Budd
Attorney, Agent, or Firm—Browning, Bushman, Zamecki & Anderson

[57] ABSTRACT

The present invention is directed to a device which simply and efficiently compensates for changes in the volume of a fluid trapped in a fluid-filled cavity between two relatively immovable housings and an elastomeric seal ring. The present invention is particularly useful in an acoustic transducer pad assembly designed for installation on logging tools used in deep boreholes in the oil and gas industry where high temperatures and pressures are experienced at downhole locations. In a presently preferred embodiment, the device comprises a transducer unit housing fixedly secured to a metal wear pad housing with an elastomeric seal disposed therebetween to define a fluid-filled cavity between adjacent portions of the housings and the seal. The seal is disposed in a groove of sufficient size to permit the required lateral expansion and contraction by deformation or extrusion of the seal in order to compensate for the expected changes in the volume of the fluid-filled cavity.

15 Claims, 2 Drawing Sheets

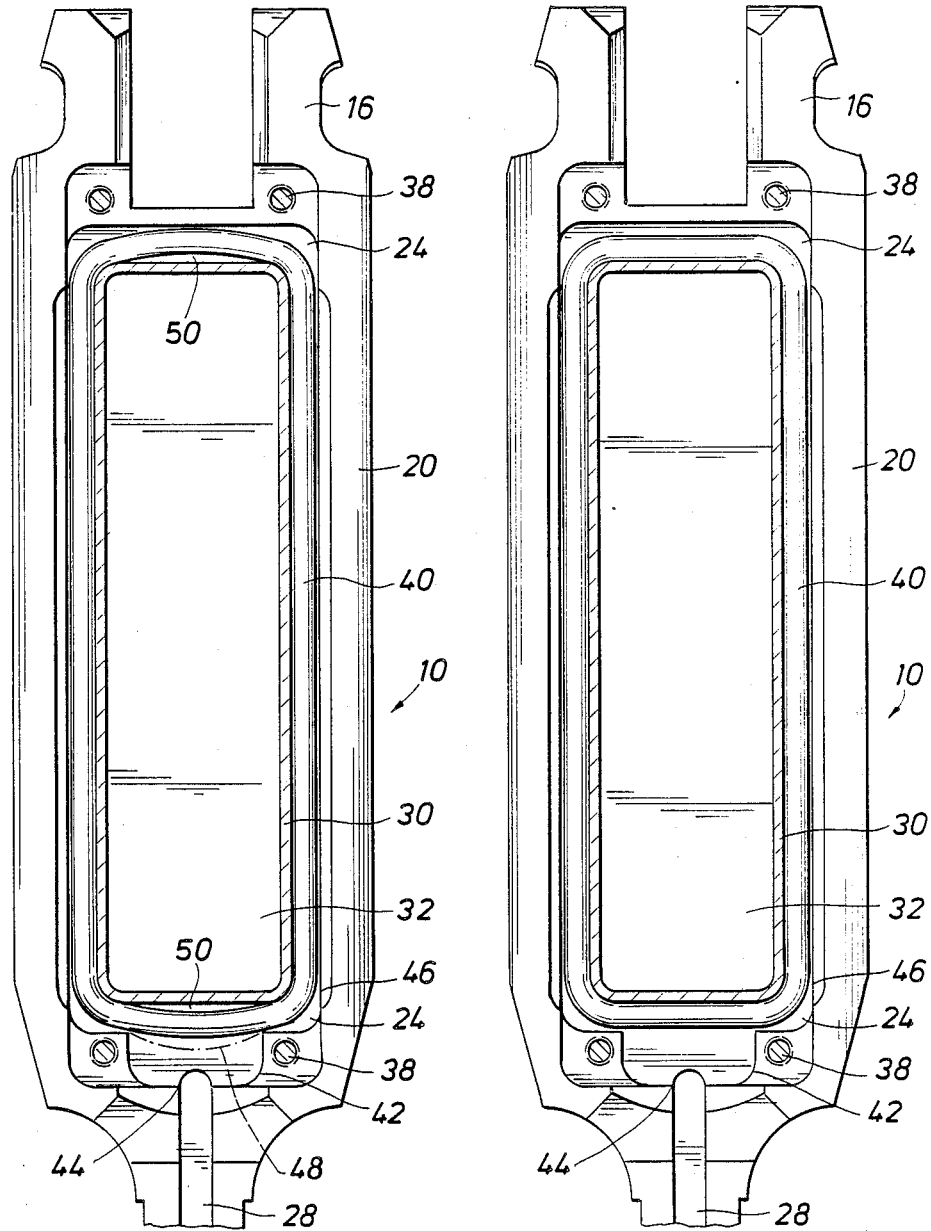

PRESSURE/TEMPERATURE COMPENSATED TRANSDUCER PAD ASSEMBLY

BACKGROUND OF THE INVENTION

1. Field of the Invention

The present invention generally relates to an apparatus having a fluid-filled cavity between two housing elements fixed relative to one another. The size of this cavity is adjustable to compensate for volumetric contraction and expansion of the fluid. More particularly, the present invention is directed to an assembly comprising a metal pad, an acoustic transducer and such a fluid-filled cavity capable of compensating for pressure and temperature changes experienced when using the assembly in a tool in a deep oil or gas well.

2. Description of the Background

Many measurements using acoustic transducers are made in the oil and gas industry in open and cased wells. Logging tools, in particular sondes from which these acoustic transducers are disposed, are passed through a borehole or a completed well to provide valuable information concerning the completed well and the formation through which the borehole has been drilled. For example, acoustic logging is often used to determine the quality of the cement bond between a casing and the surrounding formation in a completed well.

In operation, these transducers are subjected to extremes of temperature and pressure. The temperature and pressure at a downhole location is generally proportional to the depth of the location. Both temperature and pressure increase with increasing depth of the well. For example, these transducers are subjected to temperatures as high as about 350° F. and pressures as high as about 20,000 psi in boreholes in typical drilling operations. However, temperatures as high as about 500° F. and pressures as high as about 25,000 psi may be encountered in deep wells drilled to depths of about 25,000 feet.

Because the surface of the borehole or the surface of the inside of the casing is rough, it is desirable to separate the acoustic transducer from the borehole by a metal pad which will absorb the wear and abrasion of use. The metal pad is generally curved on one side for contact with the borehole or the inside wall of the casing and is typically provided with a recess on the other side into which the acoustic transducer is secured To prevent the entrance of abrasive drilling fluids between the transducer and the pad and in order to provide improved acoustic transmission between the acoustic transducer and the pad, the recess is typically filled with a protective oil prior to installation of the transducer into the recess of the pad, resulting in a thin layer of oil being trapped at the contact surface between the transducer and pad and in a small reservoir surrounding the contact surface This trapped oil expands and contracts in response to changes in the pressure and temperature in accord with its known coefficients of expansion. For example, the volume occupied by the trapped oil increases at the high temperatures encountered downhole in oil and gas wells. In typical downhole logging operations, the volume occupied by this protective oil increases by approximately 10–12 percent as the temperature increases from ambient to about 350° F. In deep wells this expansion may be as much as about 15–20 percent at temperatures of about 500° F. The drastic increases in pressure encountered downhole also affect changes in the volume of these protective oils, although the effect of pressure changes on these liquids is not so significant as the effect of temperature changes.

However, early designs for acoustic transducers used in logging tools downhole made no provision for these changes in volume of the trapped oil. Although these changes were taken into account in some later systems by inclusion of various devices, including mechanical bellows, pistons or diaphragms, a simple and satisfactory compensation system was not developed. Each of the prior devices suffers from one or more major drawbacks. Some prior transducer assemblies did not address or compensate for the problem created by the changing volume of the trapped oil. Other assemblies which included devices which addressed this problem and attempted to compensate for it were complex and expensive to construct and maintain Accordingly, there has been a long felt but unfulfilled need within the oil and gas industry for a simple, effective, economical and reliable apparatus for compensating for this expected change in fluid volume

SUMMARY OF THE INVENTION

The present invention provides a new and improved apparatus for compensating for the change in volume of the fluid filling a closed cavity between two housing members which are fixed relative to one another. The device of the present invention is particularly useful in the construction of acoustic transducer pad assemblies for use in downhole logging tools in the oil and gas drilling industry In a presently preferred embodiment, a first housing comprises a metal pad convexly curved on one side for improved contact with a borehole wall or the inside of casing cemented in a borehole. Opposite the convex surface is another surface for mating engagement with a second housing comprising an acoustic transducer unit. In the presently preferred embodiment, this mating surface of the metal pad is the bottom of a recess in the surface of the pad opposite the convex surface. The recess is designed to receive and protect at least a major portion of the acoustic transducer unit. The device further comprises means for securing the acoustic transducer unit to the metal pad to prevent relative movement of the pad and transducer.

The device further comprises a continuous strip of an elastomeric material disposed between the metal pad and the acoustic transducer unit about the periphery of the recess. In the preferred embodiment, the continuous strip is a conventional elastomeric 0-ring seal or other elastomeric seal in the desired configuration. Such a configuration defines a cavity between the metal pad, the acoustic transducer unit and the continuous strip of elastomeric material. A fluid suitable for use in the harsh downhole environment fills this cavity. In the presently preferred embodiment, this fluid is a conventional lubricating or protective oil and the elastomeric seal is an O-ring of an appropriate oil-resistant synthetic rubber.

Expansion or contraction of the fluid filling the cavity is compensated by deformation or extrusion of the elastomeric material between the metal pad and transducer unit. In the presently preferred embodiment where the elastomeric material is disposed in a groove defined by the exterior of the acoustic transducer unit and the second recess in the metal pad, this groove must be sufficiently large to accommodate the expected expansion. Accordingly, this groove is designed to permit lateral movement by deformation or extrusion of one or more portions of the elastomeric material in response to changes in volume of the fluid-filled cavity resulting from temperature changes or pressure differentials across the seal The apparatus of the present invention provides a simple and effective means for compensating for changes in the volume of a fluid in a fluid-filled cavity between two relatively fixed housings The present invention provides a simple device permitting deformation or extrusion of an elastomeric material disposed between first and second housings which have been securely fixed in constant relative position, preferably the metal pad and acoustic transducer unit of an acoustic transducer assembly in a downhole tool, in order to compensate for volumetric changes of the protective fluid in a fluid-filled cavity defined by the elastomeric material and surfaces on the first and second housings. This device is simple, economical, effective and efficient. These and other meritorious features and advantages of the present invention will be more fully appreciated from the following detailed description and claims.

BRIEF DESCRIPTION OF THE DRAWINGS

Other features and intended advantages of the present invention will be more readily apparent by the references to the following detailed description in connection with the accompanying drawings, wherein:

FIG. 3 is a cross-sectional illustration through the line 3—3 of FIG. 1 of a pressure/temperature compensated acoustic transducer assembly in accord with the present invention;

FIG. 4 is an illustration of a pressure/temperature compensated acoustic transducer assembly in accord with the present invention and in partial cross section to illustrate the elastomeric O-ring partially deformed or extruded to compensate for increased volume in the fluid-filled cavity; and FIG. 5 is an illustration of a pressure/temperature compensated acoustic transducer pad assembly in accord with the present invention and in partial cross section to illustrate the elastomeric O-ring in a less deformed or extruded state to provide a smaller fluid-filled cavity.

While the invention will be described in connection with the presently preferred embodiment, it will be understood that it is not intended to limit the invention to this embodiment. On the contrary, it is intended to cover all alternatives, modifications and equivalents as may be included in the spirit of the invention as defined in the appended claims.

DETAILED DESCRIPTION OF THE PREFERRED EMBODIMENT

The present invention is directed to an apparatus useful for compensating for the changing volume of a fluidfilled cavity as a result of changes in the pressure and the temperature of the environment in which the apparatus including the cavity is found. The present invention is particularly useful for providing a simple, economic, effective and efficient means for compensating for pressure/temperature induced changes in the volume of a protective fluid contained in a fluid-filled cavity in or about the interface of an acoustic transducer and a protective metal pad in an acoustic transducer assembly for use with downhole logging tools.

Figure 1:
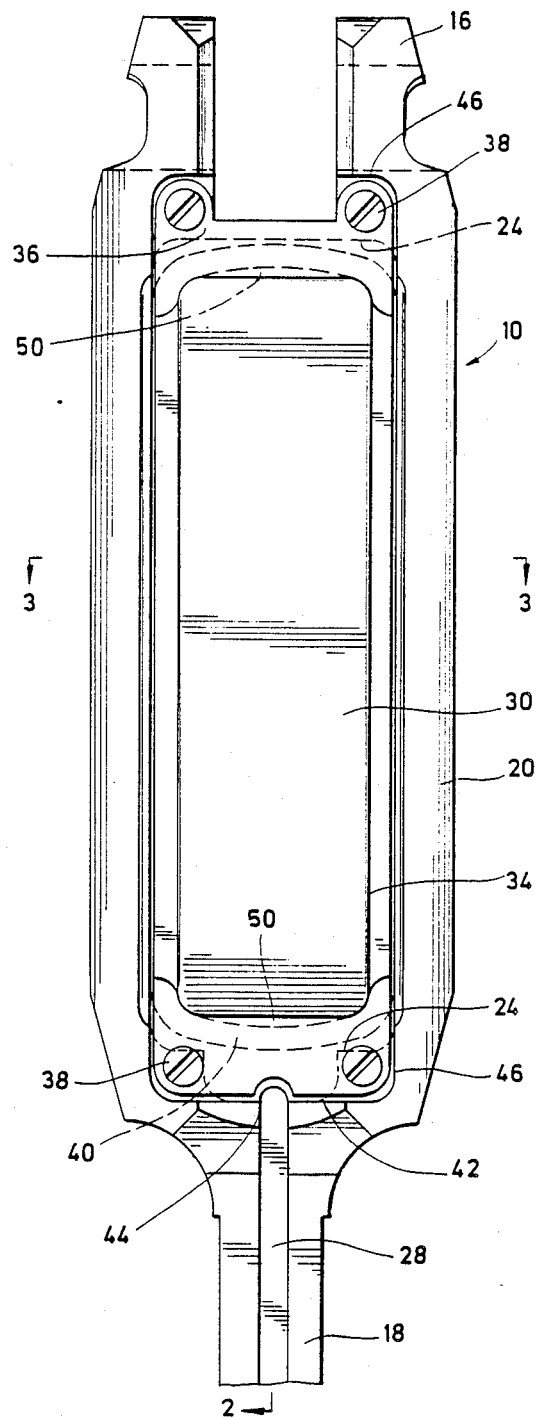
FIG. 1 is a front illustration of a pressure/temperature compensated acoustic transducer pad assembly in accord with the present invention.
Figure 2:
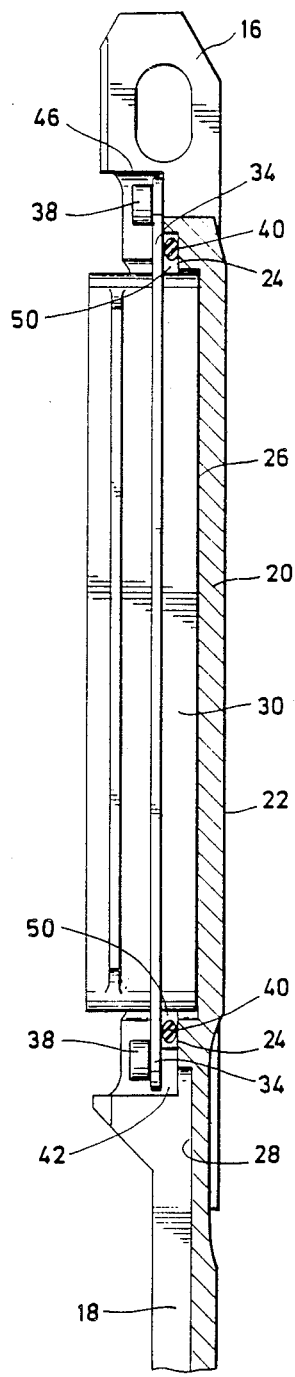
FIG. 2 is a side illustration through the line 2—2 of FIG. 1 of a pressure/temperature compensated acoustic transducer assembly, in accord with the present invention.

FIGS. 1–5 illustrate an exemplary acoustic transducer pad assembly 10 incorporating the principles of the present invention. In the exemplary illustration, transducer pad assembly 10 is disposed at the end of an arm 18. Transducer pad assembly 10 comprises an assembly housing or metal pad 20 convex on one face 22 for improved contact with the inside wall of a borehole or a casing cemented in the borehole. The assembly 10 includes at the end opposite arm 18 one side of a hinge mechanism 16. In an exemplary embodiment, a second transducer pad assembly (not illustrated), substantially identical to transducer pad assembly 10, is positioned at the opposite end of arm 18 to provide a device which is hinged at both ends for attachment to a conventional logging tool. This arrangement permits articulated movement of the pair of transducer pad assemblies 10 between a compact, retracted position permitting the logging tool to be rapidly moved through a borehole and an expanded position permitting the transducer pad assemblies 10 to contact the borehole or the inside wall of casing cemented in the borehole to produce an acoustic log of the well. For a downhole acoustic logging tool incorporating such a device, see our co-pending U.S. patent application Ser. No. 934673 filed Nov. 25, 1986 entitled "Articulated Transducer Pad Assembly for Acoustic Logging Tool" which is incorporated herein by reference. The surface of metal pad 20 opposite convex face 22 includes a mounting recess 46 within which is disposed a deeper, but smaller O-ring receiving recess 24 within which is disposed a still deeper, but smaller transducer receiving recess 26.

Transducer pad assembly 10 further comprises a transducer housing 30 within which is disposed a conventional acoustic transducer 32 for producing acoustic pulses. The transducer housing 30 includes extending about the periphery thereof a pressure flange 34 used for securing transducer housing 30 to metal pad 20 and for applying pressure to an elastomeric 0-ring seal 40. Flange 34 extends around the exterior periphery of transducer housing 30 and is wider at the ends 36 to provide locations for screws 38 to secure the transducer housing 30 to metal pad 20.

Elastomeric O-ring seal 40 constructed of any conventional oil resistant elastomer designed for use in high temperature, downhole drilling environments is disposed in the groove formed by transducer housing 30 and O-ring receiving recess 24 in metal pad 20. When pad 20, housing 30 and seal 40 are so disposed, a small cavity 50 is formed in the space between seal 40, transducer housing 30 and metal pad 20. However, after installation of seal 40, but before installation of housing 30, a small quantity of protective oil is disposed in recess 26. Accordingly, cavity 50 becomes filled with this oil as transducer housing 30 is mated to metal pad 20 and secured thereto with screws 38. As screws 38 are tightened during assembly, excess oil escapes from cavity 50 around seal 40 until the securing pressure is sufficient to provide a seal. The remaining oil is then trapped in cavity 50 to provide a barrier to protect the interface between the acoustic transducer unit 32 with the bottom of recess 26 of metal pad 20 from abrasive drilling fluids and to improve the acoustic coupling between transducer unit 32 and metal pad 20.

FIGS. 4 and 5 illustrate, in partial cross section with seal 40 exposed, a pressure/temperature compensated transducer pad assembly 10 in accord with the present invention as the assembly would appear in a borehole and at the surface, respectively FIG. 5 illustrates the position of seal 40 at ambient conditions where seal 40 conveniently fits snugly around the exterior circumference of transducer housing 30 providing a cavity 50. In fact, cavity 50 comprises only the volume of protective oil providing a film between the mating faces of transducer unit 32 and the bottom of transducer receiving recess 26 together with the oil trapped between elastomeric seal 40 and the exterior circumference of transducer housing 30. FIG. 4 illustrates, in partial cross section to reveal seal 40, a transducer pad assembly 10 in accord with the present invention as it would appear in the high temperature environment of a borehole. FIG. 4 illustrates the deformation or extrusion of the ends of seal 40 to compensate for the increased volume of the trapped oil in cavity 50. FIGS. 4 and 5 further illustrate that the groove containing seal 40 and formed by 0-ring receiving recess 24 and the exterior of transducer housing 30 is sufficiently large to permit deformation or extrusion of seal 40 to accommodate the expected degree of expansion of the oil trapped within cavity 50. However, in a preferred embodiment, recess 24 further includes at one end thereof a conduit recess 42 from which exits relief conduit 28. Excessive expansion of the fluid volume within cavity 50 causes deformation or extrusion of seal 40 into conduit 42 as illustrated in FIG. 4 at ghosted image 52. The continued expansion of the fluid in cavity 50 and the resulting deformation or extrusion of seal 40 beyond juncture 44 of conduit recess 42 with relief conduit 28 permits fluid escape from cavity 50 into relief conduit 28 and venting to the exterior of the assembly 10. The pressure inside cavity 50 is thus relieved and the integrity of seal 40 is maintained.

The foregoing description of the invention has been directed in primary part to a particular preferred embodiment in accordance with the requirements of the patent statutes and for purposes of explanation and illustration. It will be apparent, however, to those skilled in the art that many modifications and changes in the specifically described apparatus may be made without departing from the scope and spirit of the invention. For example, Applicants have illustrated and described a device wherein an elastomeric O-ring seal 40 is disposed in a single plane and in which all permissible deformation or extrusion of the seal 40 is in the same plane. However, those skilled in the art would be aware that a continuous strip of elastomeric, sealing material could be disposed in a plurality of planes between irregularly shaped, but mating housings. Such a seal could be provided with one or more areas permitting extrusion or deformation to compensate for changes in the volume of a fluid trapped within the fluid-filled cavity between the housings and the elastomeric seal. Although Applicants believe that the disclosed apparatus provides the simplest, most economical and reliable device for use with conventional transducer housing assemblies, those skilled in the art will appreciate that many other configurations having the described characteristics may produce the same results. Therefore, the invention is not restricted to the particular form of construction and method illustrated and described, but covers all modifications which may fall within the scope of the following claims.

It is Applicants' intention in the following claims to cover all modifications and variations as fall within the true spirit and scope of the invention.

What is claimed is:

1. A transducer pad assembly, comprising:
   a housing having a recess for receiving a transducer insert therein, said recess having a substantially flat bottom;
   a transducer insert for disposition in said recess, said insert having a transmission surface of substantially the same shape as said bottom for mating placement and cooperation therewith;
   a continuous strip of elastomeric material disposed between said housing and said insert about the periphery of said recess;
   means for securing said insert in said recess in a fixed position relative to said housing for producing a closed cavity defined at least in part by said bottom of said recess, said transmission surface of said insert and said continuous strip of elastomeric material; and
   an oil filling said cavity,
   said continuous strip of elastomeric material being deformable to accommodate changes in the volume of said oil filling said cavity.

2. The transducer pad assembly of claim 1 wherein said continuous strip of elastomeric material is disposed in a groove defined by said housing and said insert, said groove being substantially closed to protect said strip and being sufficiently large to accommodate said deformation of said strip.

3. The transducer pad assembly of claim 2 wherein said continuous strip of elastomeric material is disposed in a plane and is deformable in said plane.

4. The transducer pad assembly of claim 3 wherein said continuous strip of elastomeric material is expansible in at least a portion of said plane.

5. The transducer pad assembly of claim 3 wherein said continuous strip of elastomeric material is extrudable in at least a portion of said plane.

6. A device including a fluid-filled cavity wherein the volume of said cavity is adjustable in response to changes in the volume of said fluid, comprising:
   a first housing having a first surface for cooperation with a second housing;
   a second housing having a mating surface for cooperation with said first surface;
   a continuous strip of elastomeric material disposed between said first and second housings about the periphery of said first surface and said mating surface;
   means securing said first and second housings to prevent relative movement thereof and to produce a closed cavity defined at least in part by said first surface, said mating surface and said continuous strip of elastomeric material; and
   a fluid filling said cavity,
   said continuous strip of elastomeric material deformable to accommodate changes in the volume of said fluid filling said cavity without relative movement of said first and second housings.

7. The device of claim 6 wherein said continuous strip of elastomeric material is disposed in a groove defined by said first and second housings, said groove being substantially closed to protect said strip and being sufficiently large to accommodate said deformation of said strip.

8. The device of claim 7 wherein at least a portion of said continuous strip of elastomeric material is disposed in a plane between said first and second housings and is deformable in said plane.

9. The device of claim 8 wherein said continuous strip of elastomeric material is expansible in said plane.

10. The device of claim 8 wherein said continuous strip of elastomeric material is extrudable in said plane.

11. The device of claim 8 wherein said continuous strip of elastomeric material is an oil-resistant, rubber O-ring.

12. The device of claim 6 wherein said first surface comprises the bottom of a recess in said first housing and said second housing comprises an insert for cooperation with said recess.

13. The device of claim 12 wherein said insert comprises an acoustic transducer pad and said mating surface comprises the transmission surface of said transducer.

14. The device of claim 13 wherein said first housing comprises a metal pad for covering and protecting said transmission surface and at least partially protecting said transducer pad.

15. The device of claim 14 wherein said fluid is an oil suitable for use at high temperatures and high pressures.

* * * * *